US008032335B2

(12) United States Patent
Martin et al.

(10) Patent No.: US 8,032,335 B2
(45) Date of Patent: Oct. 4, 2011

(54) EVALUATING MAGNETIC RESONANCE SPECTRA

(75) Inventors: Diego R. Martin, Atlanta, GA (US); Xiaoping Hu, Tucker, GA (US); Nashiely Pineda-Alonso, Saint Ouen (FR); Puneet Sharma, Atlanta, GA (US)

(73) Assignee: Emory University, Atlanta, GA (US)

( * ) Notice: Subject to any disclaimer, the term of this patent is extended or adjusted under 35 U.S.C. 154(b) by 442 days.

(21) Appl. No.: 12/248,508

(22) Filed: Oct. 9, 2008

(65) Prior Publication Data

US 2009/0276187 A1 Nov. 5, 2009

Related U.S. Application Data

(60) Provisional application No. 61/126,259, filed on May 2, 2008.

(51) Int. Cl.
*G01R 33/54* (2006.01)
*G01F 19/00* (2006.01)

(52) U.S. Cl. ........ 702/189; 702/190; 702/193; 324/300; 324/301; 324/307; 324/309; 600/407; 600/408; 600/409; 600/410; 600/411; 600/412; 600/413; 600/414; 600/415

(58) Field of Classification Search .................. 702/189, 702/190, 193; 324/300, 301, 307, 309; 600/407–415
See application file for complete search history.

(56) References Cited

U.S. PATENT DOCUMENTS

| 5,486,762 | A | * | 1/1996 | Freedman et al. | ............ 324/303 |
| 5,879,299 | A | * | 3/1999 | Posse et al. | .................... 600/410 |
| 2010/0286500 | A1 | * | 11/2010 | Ruhm | ............................ 600/410 |

OTHER PUBLICATIONS

Alustiza, JM et al. MR Quantification of Hepatic Iron Concentration. *Radiology.* 230:479-484 (2004).
Angulo, P. Nonalcoholic Fatty Liver Disease. *N Engl J Med.* 346:1221-1231 (2002).
Bernard, CP et al. Comparison of Fat Quantification Methods: A Phantom Study at 3.0T. *J Magn Reson Imaging.* 27(1):192-7 (Jan. 2008).
Bluml, S et al. Spin-Lattice Relaxation Time Measurement by Means of a TurboFLASH technique. *Magn Reson Med.* 30:289-295 (1993).
Carneiro, Aao et al. Liver Iron Concentration Evaluated by Two Magnetic Methods: Magnetic Resonance Imaging and Magnetic Susceptometry. *Magnetic Resonance in Medicine.* 54:122-128 (2005).
Chan, DC et al. Measurement of Liver Fat by Magnetic Resonance Imaging: Relationship with Body Fat Distribution, Insulin Sensitivity and Plasma Lipids in Healthy Men. *Diabetes Obes Metab.* 8:698-702 (Nov. 2006).
Chang, JS et al. Opposed-phase MRI for Fat Quantification in Fat-Water Phantoms with 1HMR Spectroscopy to Resolve Ambiguity of Fat or Water Dominance. *AJR Am J Roetgenol.* 187:W103-W106 (Jul. 2006).
Chu, Z et al. MRI Measurement of Hepatic Magnetic Susceptibility—Phantom Validation and Normal Subject Studies. *Magnetic Resonance in Medicine.* 52:1318-1327 (2004).

(Continued)

*Primary Examiner* — Sujoy Kundu
(74) *Attorney, Agent, or Firm* — McKeon, Meunier, Carlin & Curfman

(57) ABSTRACT

Provided are methods, systems and computer program products evaluating magnetic resonance (MR) signals from a sample. The methods and systems can be used to evaluate MR signals from various constituents (e.g., metabolites, macromolecules) of the sample.

17 Claims, 5 Drawing Sheets

OTHER PUBLICATIONS

Cortez-Pinto, H. Non-alcoholic Fatty Liver Disease/ Non-alcoholic Steatohepatitis (NAFLD/NASH): Diagnosis and Clinical Course. *Best Practice & Research Clinical Gastroenterology.* 18:1089-1104 (2004).

De Bazelaire, CM et al. MR Imaging Relaxation Times of Abdominal and Pelvic Tissues Measured In Vivo at 3.0 T: Preliminary Results. *Radiology.* 230(3):652-9 (Mar. 2004).

Dixon, WT. Simple Proton Spectroscopic Imaging. *Radiology.* 153:189-194 (1984).

Fishbein, MH et al. Introduction of fast MR Imaging in the Assessment of Hepatic Steatosis. *Magn Reson Imaging.* 15:287-293 (1997).

Fishbein, MH et al. Rapid MRI Using a Modified Dixon Technique: a Non-Invasive and Effective Method for the Detection and Monitoring of Fatty Metamorphosis of the Liver. *Pediatr Radiology.* 31:806-809 (2001).

Fishbein, MH et al. The Spectrum of Fatty Liver in Obese Children and the Relationship of Serum Aminotransferases to Severity of Steatosis. *J. Pediatr Gastroenterol Nutr.* 36:54-61 (2003).

Garbow, Jr. In Vivo MRS Measurement of Liver Lipid Levels in Mice. *Journal of Lipid Research.* 45:1364-1371 (2004).

Glover, GH. Multipoint Dixon Technique for Water and Fat Proton and Susceptibility Imaging. *J Magn Reson Imaging.* 1:521-530 (1991).

Glover, GH et al. Three-Point Dixon Technique for True Water/Fat Decomposition with Bo Inhomogeneity Correction. *Magn Reson Med.* 18:371-383 (1991).

Goldberg, MA et al. Value of T1 and T2 Relaxation Times from Echoplanar MR Imaging in the Characterization of Focal Hepatic Lesions. *AJR Am J Roentgenol.* 160(5):1011-7 (May 1993).

Heiken, JP et al. Fatty Infiltration of the Liver: Evaluation by Proton Spectroscopic Imaging. *Radiology.* 157(3):707-10 (Dec. 1985).

Hollingsworth, KG et al. Low-Carbohydrate Diet Induced Reduction of Hepatic Lipid Content Observed with a Rapid Non-Invasive MRI Technique. *Br J Radiol.* 79: 712-715 (2006).

Hussain, Hk et al. Hepatic Fat Fraction: MR Imaging for Quantitative Measurement and Display—Early Experience. *Radiology.* 237(3):1048-55. (Dec. 2005). Epub Oct. 19, 2005.

Isobe, T et al. Quantification of Cerebral Metabolites in Glioma Patients with Proton MR Spectroscopy Using T2 Relaxation Time Correction. *Magn Reson Imaging.* 20(4): 343-9 (May 2002).

Jackson, JA et al. Improvements in the Clinical Utility of Calculated T2 Images of the Human Brain. *Magn Reson Imaging.* 3(2):131-43 (1985).

Kim, H et al. Comparative MR Study of Hepatic Fat Quantification Using Single-Voxel Proton Spectroscopy, Two-Point Dixon and Three Point IDEAL. *Magnetic Resonance in Medicine.* 59:521-527 (2008).

Kreis, R. Quantitative Localized 1H MR Spectroscopy for Clinical Use. *Journal of Progress in Nuclear Magnetic Resonance Spectroscopy.* 31:155-195 (1997).

Longo, R et al. Fatty Infiltration of the Liver. Quantification by 1H Localized Magnetic Resonance Spectroscopy and Comparison with Computed Tomography. *Invest Radiol.* 28(4):297-302 (Apr. 1993).

Longo, R et al. Proton MR Spectroscopy in Quantitative In Vivo Determination of Fat Content in Human Liver Steatosis. *J Magn Reson Imaging.* 5(3):281-5 (May-Jun. 1995).

Machann, J et al. Hepatic Lipid Accumulation in Healthy Subjects: A Comparative Study Using Spectral Fat-Selective MRI and Volume-Localized 1H-MR Spectroscopy. *Magnetic Resonance in Medicine.* 55(4):913-917 (Apr. 2006).

Marsman, WA. Use of Fatty Donor Liver is Associated with Diminished Early Patient and Graft Survival. *Transplantation.* 62:1246-1251 (1996).

Provencher, SW. Automatic Quantitation of Localized in vivo 1H Spectra with LCModel. *NMR Biomed.* 14:260-264 (2001).

Radetti, G et al. Non-Alcoholic Fatty Liver Disease in Obese Children Evaluated by Magnetic Resonance Imaging. *Acta Pediatrica.* 95:833-837 (2006).

Reeder, SB et al. Multicoil Dixon Chemical Species Separation with an Iterative Least Squares Estimation Method. *Magn Reson Med.* 51:35-45 (2004).

Schuchmann, S. et al. Non-Invasive Quantification of Heptic Fat Fraction by Fast 1.0, 1.5, and 3.0 T MR Imaging. *Eur J Radiol.* 62:416-422 (Jun. 2007). Epub Jan. 30, 2007.

St. Pierre T.G. et al. Noninvasive Measurement and Imaging of Liver Iron Concentrations Using Proton Magnetic Resonance. *Blood.* 105:855-861 (2005).

Szczepaniak, LS et al. Measurement of Intracellular Triglyceride Stores by H Spectroscopy: Validation In Vivo. *Am J Physiol Endocrinol Metab.* 276(5 Pt 1):E977-E989 (May 1999).

Szczepaniak, LS et al. Magnetic Resonance Spectroscopy to Measure Hepatic Triglyceride Content: Prevalence of Hepatic Steatosis in the General Population. *Am J Physiol Endocrinol Metab.* 288(2): E462-8 (Feb. 2005).

Thampanitchawong, P. et al. Liver Biopsy: Complications and Risk Factors. *World J Gastroenterol.* 5:301-304 (1999).

Thomas, EL et al. Hepatic Triglyceride Content and its Relation to Body Adiposity: a Magnetic Resonance Imaging and Proton Magnetic Resonance Spectroscopy Study. *Gut.* 54(1):122-7 (Jan. 2005).

Thomsen, C et al. Quantification of Liver Fat Using Magnetic Resonance Spectroscopy. *Magn Reson Imaging.* 12(3):487-95 (1994).

Voskaridou, E et al. Magnetic Resonance Imaging in the Evaluation of Iron Overload in Patients with Beta Thalassaemia and Sickle Cell Disease. *British Journal of Haematology.* 126:736-742 (2004).

Wang, ZJ et al. Evaluation of Iron Overload by Single Voxel MRS Measurement of Liver T2. *Journal of Magnetic Resonance Imaging.* 15: 395-400 (2002).

Westphalen, Aca et al. Liver Fat: Effect of Hepatic Iron Deposition on Evaluation with Opposed-Phase MR Imaging. *Radiology.* 242(2):450-455 (2007).

Wood, JC. Magnetic Resonance Imaging Measurement of Iron Overload. *Curr Opin Hematol.* 14:183-190 (2007).

\* cited by examiner

EVALUATING MAGNETIC RESONANCE SPECTRA

This application claims priority to U.S. Provisional Application 61/126,259, filed May 2, 2008, which is incorporated herein by reference in its entirety.

BACKGROUND

The rapid and accurate assessment of samples, such as biological samples can provide information regarding constituents of the samples, can facilitate disease detection in individuals, and can provide valuable insights into biology and pathological conditions.

SUMMARY

Provided are methods, systems and computer program products that relate to evaluating magnetic resonance (MR) signals from a sample. The methods and systems can be used to evaluate MR spectra from various constituents (e.g., metabolites, macromolecules) of samples, such as biological samples like human or animal tissue.

For example, included is a method for quantifying content of a spectral component of a magnetic resonance signal from a sample comprising estimating a transverse relaxation property for at least two spectral components of the sample. The transverses relaxation properties can be estimated by applying a series of temporally spaced radio frequency pulses and at least one magnetic field gradient to the sample; detecting a magnetic resonance signal from the sample at multiple predefined measurement times; obtaining a frequency-domain representation of the detected magnetic resonance signal at each measurement time, wherein each frequency-domain representation comprises a plurality of peaks, each peak corresponding to a spectral component of the sample; determining an area beneath at least two peaks in each frequency-domain representation of the magnetic resonance signal; and performing a fitting routine on the determined peak areas to estimate a transverse relaxation property for at least two spectral components. The estimated transverse relaxation properties can be used to extract equilibrium signal intensities for at least two of the spectral components and a ratio can be calculated of the equilibrium signal intensity extracted for a selected spectral component to a sum of all the extracted spectral component equilibrium signal intensities to quantify the content of the selected spectral component of the signal from the sample.

The methods also include a method of estimating a transverse relaxation property for at least two spectral components of a sample comprising applying a series of temporally spaced radio frequency pulses and at least one magnetic field gradient to the sample; detecting a magnetic resonance signal from the sample at multiple predefined measurement times; obtaining a frequency-domain representation of the detected magnetic resonance signal at each measurement time, wherein each frequency-domain representation comprises a plurality of peaks, each peak corresponding to a spectral component of the sample; determining an area beneath at least two peaks in each frequency-domain representation of the magnetic resonance signal; and estimating the transverse relaxation property for at least two spectral components by performing a fitting routine on the determined peak areas.

The methods also include a method for quantifying a content of a spectral component within a magnetic resonance signal from a sample comprising obtaining a magnetic resonance signal from the sample; obtaining a transverse relaxation rate for at least two spectral components in signal; extracting from the signal an equilibrium signal intensity for at least two spectral components; and calculating a ratio of the equilibrium signal intensity for a first spectral component to a sum of all calculated spectral component equilibrium signal intensities to quantify the content of the first spectral component of the signal from the sample.

A computer program product is also provided that is encoded on a computer-readable medium and that is operable to cause a data processing apparatus to perform operations comprising applying to a sample a series of three radio frequency pulses. The series comprises a first pulse having a sufficient amplitude and duration to cause proton spins in the sample to rotate about 90 degrees around an axis applying at least one magnetic field gradient to the sample; a second pulse having a sufficient amplitude and duration to cause the proton spins in the sample to rotate about 90 degrees around an axis; and a third pulse having a sufficient amplitude and duration to cause the proton spins in the sample to rotate about 90 degrees around an axis. The series of pulses can be repeated three, four, or five times at a temporal spacing that permits measurement of a transverse relaxation rate of the sample.

A computer program product is also provided that is encoded on a computer-readable medium and is operable to cause a data processing apparatus to perform operations comprising applying to a sample a series of three radio frequency pulses The series comprises a first pulse having a sufficient amplitude and duration to cause proton spins in the sample to rotate about 90 degrees around an axis applying at least one magnetic field gradient to the sample; a second pulse having a sufficient amplitude and duration to cause the proton spins in the sample to rotate about 180 degrees around an axis; and a third pulse having a sufficient amplitude and duration to cause the proton spins in the sample to rotate about 180 degrees around an axis. The series of pulses can be repeated three, four, or five times at a temporal spacing that permits measurement of a transverse relaxation rate of the sample.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
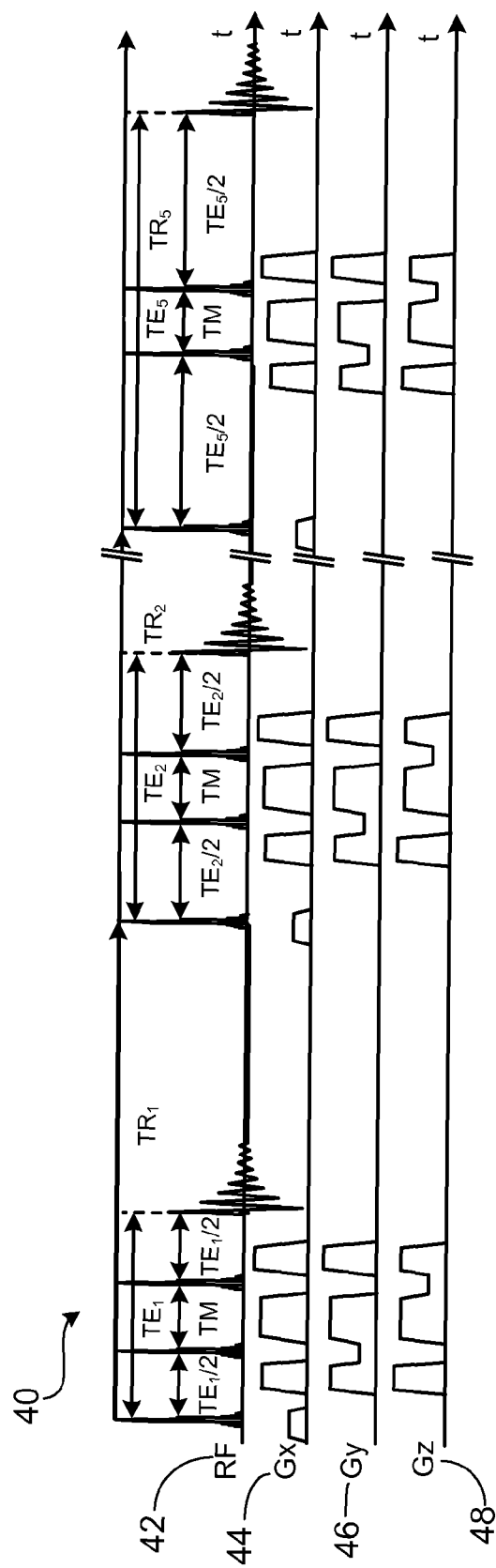
FIG. 1 is a timing diagram of a magnetic resonance pulse sequence.

The following detailed description should be read with reference to the drawings in which similar elements in different drawings are numbered the same. The drawings, which are not necessarily to scale, depict illustrative embodiments and are not intended to limit the scope of what is claimed. Provided are methods, systems and computer program products related to evaluating magnetic resonance (MR) spectra from a sample. The methods, systems and computer program products can be used to evaluate MR spectra representative of various constituents found in a sample. A constituent of a sample refers to a part of the sample that can produce an MR signal. For example, when an MR signal is measured from a region of a sample, constituents, such as metabolites or macromolecules, can contribute to a component of an MR spectrum obtained from the measured MR signal. By evaluating MR spectra representative of constituents found in the sample, the amount or percentage of a constituent in the sample can be quantified.

A content (e.g., an amount or a percentage) of a constituent of a sample can be quantified by estimating how much of the MR spectrum is occupied by a component (e.g., a peak) that corresponds to the constituent of the sample. For example, a content of a constituent can be estimated by comparing the area occupied by the spectral component that corresponds to the constituent to the total area occupied by other spectral components. Said another way, a spectral component of an MR signal is representative of a constituent of a sample, and by quantifying the content of the spectral component, a quantity of the constituent in the sample can be determined, estimated or measured. For example, the amount or percentage of fat in liver tissue can be estimated.

The methods can further be used to assess the content of a substance having a positive magnetic susceptibility in the sample. For example, the amount of iron in a sample can be determined or estimated. Thus, the methods can be optionally used to assess both the content of lipid and iron in a sample such as liver. Since both lipid content and iron content are often clinically relevant in conditions such as hepatitis, liver fibrosis, and liver cirrhosis, the methods can be used to assess liver diseases and abnormalities in clinical settings.

Because liver and the constituents of liver can be assessed using the methods, one non-limiting example of a sample comprises in vivo or ex vivo liver tissue, and the methods can be used to assess fat and iron content of the liver tissue sample. A sample, however, is not limited to liver and a sample can be any composition or structure in which a MR signal can be generated. Optionally, the sample comprises human or non-human animal tissue and the methods can be used to assess MR spectra from a subject including human and non-human animals. Moreover, a sample can comprise tissue removed from an animal or human and the methods can be performed on the sample ex vivo.

Quantifying the content of a spectral component of the MR signal from a sample includes estimating a transverse relaxation property for at least two spectral components of the sample. The estimated transverse relaxation properties are then used to extract equilibrium signal intensities for the spectral components. The equilibrium signal intensities are used to quantify the content of a selected spectral component.

To estimate the transverse relaxation property for the spectral components, a series of temporally spaced radio frequency (RF) pulses and at least one magnetic field gradient are applied to the sample. FIG. 1 is a schematic diagram illustrating an example MR pulse sequence that shows a timing of transmitted RF pulses, which are used to excite protons within a sample, and applied magnetic field gradients, which can be used to select a voxel or a volume element within a sample. Signals acquired from an MR experiment that uses a pulse sequence can be used for estimating a transverse relaxation property for at least two spectral components of the sample. A pulse sequence is a set of instructions that are executed by a magnetic resonance system. A pulse sequence can reside in a computer memory and can manage the timing of transmitted radio frequency and gradient pulses as well as collection of signals from the MR scanner.

The pulse sequence 40 shown represents an MR acquisition that can be used to estimate a relaxation property (e.g., the transverse relaxation rate R2) for a spectral component representative of a constituent of the sample. For example, the pulse sequence 40 can be used to estimate the R2 of a water constituent of the sample. The water component of a measured MR spectrum typically occupies the largest fraction of the spectrum. As such, to quantify the content of a sample constituent besides water, the area of at least the water component should also be quantified so that a ratio can be calculated.

The pulse sequence timing schematic includes a graph that represents RF transmissions. The RF pulses can be selective or non-selective. The RF pulses can be of an amplitude and duration that causes the proton spins in the sample to rotate a specified angle (e.g., about 90 degrees, about 180 degrees) around a given axis (e.g., x axis, y axis, z axis). Thus, optionally, the series of radiofrequency pulses can include a first pulse having a sufficient amplitude and duration to cause the proton spins in the sample to rotate about 90 degrees around an axis, a second pulse having a sufficient amplitude and duration to cause the proton spins in the sample to rotate about 90 degrees around an axis, and a third pulse having a sufficient amplitude and duration to cause the proton spins in the sample to rotate about 90 degrees around an axis. The series of radiofrequency pulses can also include a first pulse having a sufficient amplitude and duration to cause proton spins in the sample to rotate about 90 degrees around an axis, a second pulse having a sufficient amplitude and duration to cause proton spins in the sample to rotate about 180 degrees around an axis, and a third pulse having a sufficient amplitude and duration to cause proton spins in the sample to rotate about 180 degrees around an axis. In any case, the series of three pulses can be optionally repeated three, four, five times or more.

Referring again to FIG. 1, the timing listed between RF pulses is abbreviated as a first echo time, TE1, a mixing time, TM, a first repetition time, TR1, a second echo time, TE2, a second repetition time, TR2, and, following a break in time, a fifth echo time, TE5, and a fifth repetition time, TR5. The repetition times optionally have a constant value (e.g., TR1=TR2 . . . =TR5=2000 ms) and the echo times span a range of times (e.g., about 2 ms-200 ms, or about 5 ms-50 ms, or about 12 ms-72 ms).

Five example repetitions of RF pulses are shown in FIG. 1, although the sequence can be repeated any number of times (e.g., three, four, five, six, seven, ten, or more). Each subsequent measurement can include an echo time that can be a different value from previous echo times. Each time the sequence is repeated, the duration of the method is lengthened by a TR and an additional data set is collected that can be used for analysis. The amount of data collected can be balanced with the length of the MR scan. Each of graphs 44, 46, and 48 represents the gradient strength along one of three orthogonal axes. The abscissa of each of the four graphs 42, 44, 46, and 48 is time.

Following application of the radio frequency pulses and magnetic field, an MR signal from the sample can be detected at multiple predefined measurement times. The measurement times are selected to sample the decay of the detected MR signal and are usually timed to correspond to an echo time. Optionally, the duration between a first radio frequency pulse in the series and a final time of the multiple predefined measurement times is no more than about 15 seconds. A frequency-domain representation of the detected magnetic resonance signal at each measurement time can then be obtained.

Figure 2:
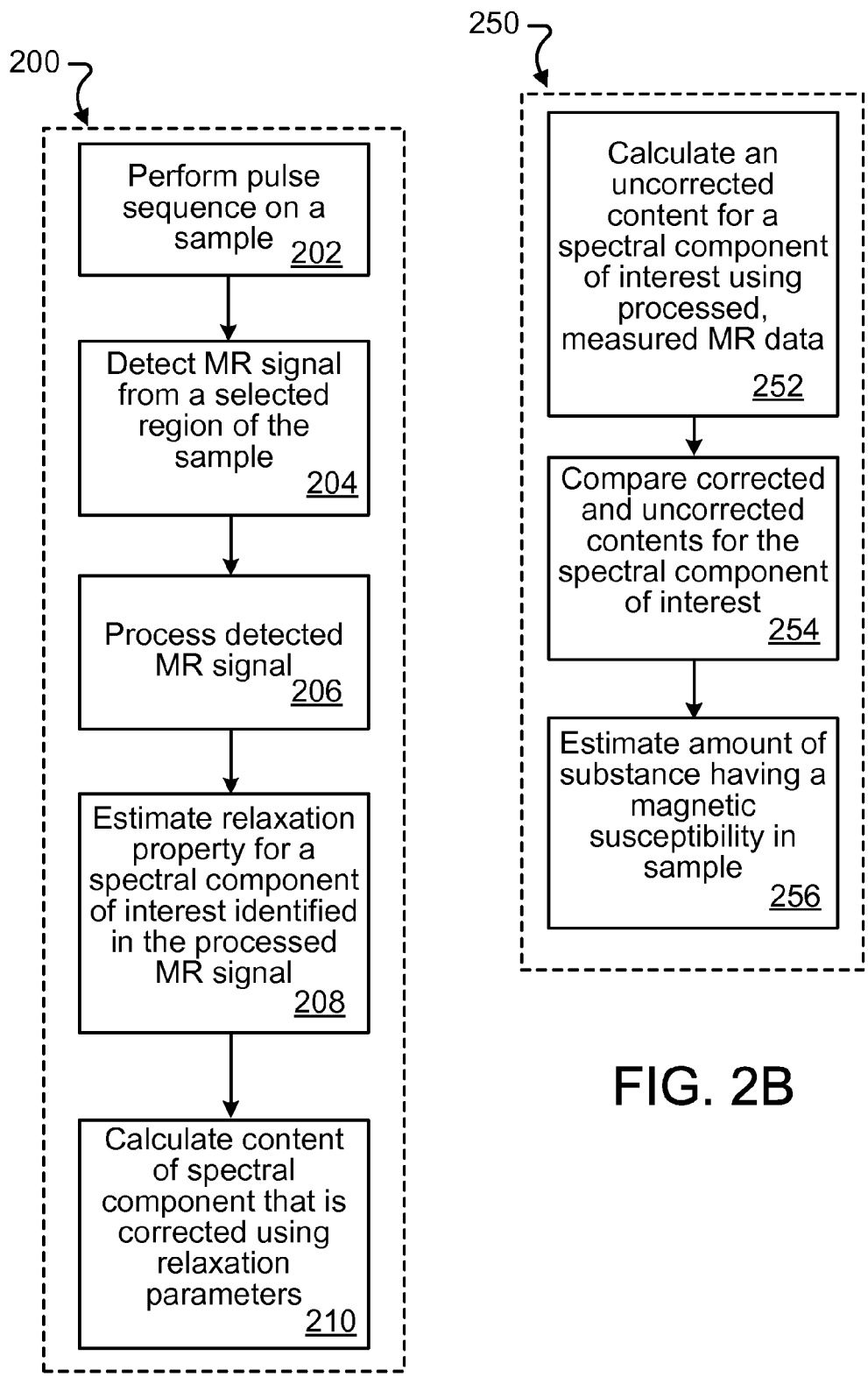
FIGS. 2A and 2B are flowcharts illustrating example MR signal acquisition and signal processing steps.

A flowchart 200 in FIG. 2A describes example MR signal acquisition and MR signal processing steps. A pulse sequence (e.g., pulse sequence 40) is performed on a sample (step 202) and the MR signal is detected from a selected region of the sample (step 204). The detected MR signal is optionally processed (step 206) and a relaxation property (e.g., the transverse relaxation rate R2) is estimated for a spectral component of interest (step 208) that is identified in the processed MR signal.

Example optional processing that can take place in step 206 include forming a frequency domain signal (e.g., by Fourier transforming the detected MR time domain signal), changing a phase of the spectrum (e.g., the real part, the imaginary part), filtering the spectrum (e.g., using a low pass filter) with a specified frequency range (e.g., about 0 to 240 Hz). Processing of the measured MR signal can be performed with a software package (e.g., MATLAB®, LCModel). (LCModel is an analysis package by S. Provencher, Oakville, Canada. See, for example *Provencher SW. Automatic quantitation of localized in vivo 1H spectra with LCModel. NMR Biomed.* 2001;14:260-264.). If the LCModel software package is used, spectrum analysis can be performed in the frequency domain using a linear combination of model spectra. A region-specific analysis can be performed by setting the "SPTYPE" variable equal to the region begin imaged (e.g., "liver-1"). The software can be used to analyze the spectra using a priori assumptions about which signals contribute to the spectrum. For example, if "liver-1" is chosen, the software assumes the signals include lipid, water, and possibly choline signals, plus possible signals in the 3.4-3.8 ppm region (sometimes attributed to glycogen and other metabolites).

To estimate a relaxation property (e.g., the transverse relaxation rate R2) for a spectral component of interest, a representation (e.g., a peak) that corresponds to the spectral component is identified in the frequency domain representation of the detected magnetic resonance signal and an area beneath the representation can be calculated (e.g., by integration). The area that corresponds to each spectral component of interest can be calculated for the MR signal that is detected at each predetermined echo time in the pulse sequence 40. R2 can be estimated for a spectral component of interest by using a fitting routine (e.g., the nlinfit function in Matlab) to fit a series of calculated areas that each correspond to a predetermined echo time. For example, a mono-exponential curve ($S=S_0*\exp(-R2*TE)$) can be used for the fitting routine, in which S represents the processed, detected MR signal, $S_0$, the equilibrium value, R2, the transverse relaxation rate, and TE, the echo time. $S_0$ suggests what amplitude would be detected for the spectral component if an MR signal could be detected at a time TE of 0.

Longitudinal relaxation rate (R1) contributions can be neglected due to the "single-shot" nature of the pulse sequence 40 (i.e., the MR signal is detected rapidly enough so that loss of signal due to longitudinal relaxation is not a concern). $S_0$ and R2 can be estimated for all experiments, and a goodness-of-fit can be calculated by computing an r-squared statistic.

Spectral components of interest can include, for example, water, lipid, or other metabolites, can be identified in the frequency domain representation or spectrum of the detected MR signal. If the spectral component of interest is present in the sample, a peak can be located in the spectrum at a corresponding frequency location that depends on the field strength of the magnetic field. A part per million (ppm) representation in which the frequency is normalized by the magnetic field can be used. Many example metabolites that can be observed are listed in Table 1 along with their corresponding ppm range (from Ross B D, Colletti P, Lin A, *MR spectroscopy of the brain: Neurospectroscopy. in Clinical Magnetic Resonance Imaging,* 3rd edition, Edelman, Hesselink, Zlatkin & Crues, eds., Saunders-Elsevier, Philadelphia, 2006, pp 1840-1910.)

TABLE 1

Metabolites Observed in MR Spectroscopy

| Target | Ppm |
|---|---|
| Lipids (brain) | About 0.9-about 1.4 |
| Lipids (liver)* | About 0 to about 3.6 |
| Lactate | about 1.3 |
| NAA | about 2.0 |
| Glutamate/GABA | about 2.2 to about 2.4 |
| Creatine | about 3.0 |
| Choline | about 3.2 |
| Myo-Inositol | about 3.5 |
| Ethanol | about 1.2 |
| Alanine | about 1.48 |
| Glucose | about 3.4 and about 3.8 |
| Mannitol | about 3.8 |
| Water | about 3.6-5.8 |

*(methylene and methyl signals of $\alpha$-$CH_2$, $(CH_2)_{n-2}$ and $CH_3$)

Optionally, a first peak of interest can be located at about 4.7 parts per million (ppm), corresponding to the spectral location for water (see Table 1). Optionally, a second peak of interest can be located between about 1 part per million (ppm) and about 1.5 ppm, which corresponds to the spectral location for lipids (see Table 1).

The equilibrium signal intensity, $S_0$, is not a detected value (as no detection of an MR signal could occur at a time of 0). The signal S, which is detected at times greater than 0, for a spectral component is smaller than the equilibrium signal intensity for the spectral component by an amount that depends on the detection time and the R2 of the spectral component.

By substituting the estimated R2 value for a spectral component of interest into the signal equation $S=S_0*\exp(-R2*TE)$, $S_0$ can be extracted for the spectral component from any signal, S, that was measured at a time TE. The equilibrium signal intensity has been corrected to remove relaxation effects (e.g., signal decay caused by transverse relaxation). As such, the pulse sequence 40 can provide an estimate of R2 as well as an equilibrium signal intensity for a spectral component of interest.

A ratio can be calculated of the equilibrium signal intensity extracted for a selected spectral component to a sum of all the extracted spectral component equilibrium signal intensities. The calculated ratio can be used to quantify the content of the spectral component of interest within a selected region of the sample. When the ratio is calculated using the equilibrium signal intensities of the spectral components, the quantified content is said to be corrected for relaxation effects.

This ratio provides a corrected content of the selected spectral component and the transverse relaxation property data (i.e., the T2 data) can be used to correct the content of the selected spectral component. Thus, corrected estimates of the concentration of targeted constituents can be obtained. The pulse sequence 40 can be referred to as a "high speed, T2-corrected, multiple echo proton MR spectroscopy acquisition" or "HISTO." A method that uses the HISTO pulse sequence (e.g., the pulse sequence 40) can be referred to as a "HISTO method" and can be used to 1) estimate transverse relaxation rates for spectral components in the detected MR signal from a region of a sample; 2) obtain an estimate of equilibrium signal intensities of the spectral components; and 3) obtain an estimate of a content of a spectral component that is not corrupted by relaxation effects.

A corrected content of a spectral component, $C_A$, can be calculated as: $C_{A,corr}=S_{0,A}/(S_{0,B}+S_{0,A})\times 100$, in which $S_{0,A}$ represents the equilibrium signal intensity for spectral component A (calculated in step 206) and $S_{0,B}$ represents the sum of equilibrium signal intensities for one or more additional identified spectral components in the spectrum (also calculated in step 206). Because the equilibrium signal intensity is used to calculate the relative spectral component content, and because estimation of this signal intensity uses knowledge of relaxation parameters (e.g., R2—which equals 1/T2), the calculated spectral component content is "T2-corrected."

A benefit for correcting detected MR signals for relaxation effects is improved accuracy and precision over uncorrected results. This can have particular implications in individuals with low lipid content levels, where significant R2 water spectral decay can falsely augment measured lipid content on traditional, uncorrected MRS sequences.

A MR signal from a spectral component (e.g., a metabolite or a macromolecule) can be attenuated or can have its phase shifted during the quantification process, especially when in the presence of substances having a magnetic susceptibility (e.g., iron). These attenuation or phase-shifting effects, which are amplified with increasing magnetic field strength, affect subsequent concentration calculations (i.e., quantification) in a nontrivial manner, especially if the relaxation rates of the multiple targets are very different from each other. In practice, in vivo relaxation rates of targets are unknown. Measuring the relaxation rates of multiple targets within a sample permits correction for the effects caused by materials having a magnetic susceptibility and to more accurately and consistently determine concentrations of biological targets.

The absolute magnitude of spectra within a voxel can be underestimated by both incomplete signal recovery between measurement periods (which is governed by a target's longitudinal relaxation rate, R1, or the longitudinal relaxation time, 1/R1) and transverse signal decay (which is governed by a target's transverse relaxation rate, R2, or the transverse relaxation time, 1/R2). Also, due to relaxation effects, the MRS signal for each constituent (e.g., water and lipid) are depressed from its equilibrium signal at a given measurement time by an amount that depends on its R2

As obesity related fatty liver disease has become the most common cause of hepatitis and liver fibrosis in developed nations, evaluation of liver lipid content is clinically important. Thus, one optional application of the described methods is to assess lipid percentage or amount in subjects with liver disease, or at risk of developing liver disease. For example, a HISTO pulse sequence can be performed on the liver of a human or non-human animal subject and spectral components, such as lipid and water, can be identified in the Fourier-transformed, phased, and filtered data. Both the transverse relaxation rate (R2) and the equilibrium signal intensity ($S_0$) can be estimated for the water and the lipid signals, as described above. Lipid content can be calculated by Lipid content=$S_{Fat}/(S_{Fat}+S_{Water})*100$ at each measured TE, as well as "TE=0" using the calculated $S_0$ values for water and lipid that were obtained through the relaxation parameter fits. Lipid content measurements using $S_0$ represent the T2-corrected lipid content.

Optionally, the selected spectral component comprises lipid and the ratio quantifies the lipid content within a selected region of the sample.

For example, for a sample that contained at least two constituents, lipid and water signals, an equation can be written to express the lipid content in terms of the R2 of each constituent:

$$LipidContent = \frac{S_{lip}}{S_{wat}+S_{lip}} = \frac{S_{0Lip}\exp(-R2_{lip}\cdot TE)}{S_{0wat}\exp(-R2_{wat}\cdot TE)+S_{0Lip}\exp(-R2_{lip}\cdot TE)}. \quad [1]$$

With TE fixed, the independent variables are $R2_{lip}$ and $R2_{wat}$. If these values are equivalent, lipid content calculations are unaffected by T2 relaxation, and any practical TE can be used. Previous hepatic lipid content investigations have shown similar R2 for water and lipid (see, for example, Longo, R. et al., *Invest Radiol*. April 1998;28(4):297-302; Szczepaniak L S, et al., *Am J Physiol Endocrinol Metab*. February 2005;288(2):E462-8; Heiken, J P, et al., Radiology. December 1985;157(3):707-10). However, if $R2_{wat}$ becomes much larger than $R2_{lip}$, as occurs in the presence of materials with a large magnetic susceptibility (such as iron), a disproportionate loss in liver water signal relative to lipid signal will result. T2-correction in this scenario can be used. As a plot of R2 against iron content is linear, and because $R2_{0fat}\approx R2_{0wat}$, equation 1 can be reduced to:

$$LipidContent = \frac{S_{0Lip}\exp(-A\cdot TE)}{S_{0Lip}\exp(-A\cdot TE)+S_{0wat}\exp(-7.8A\cdot TE)}, \quad [2]$$

where $A=r_{2fat}\cdot[Fe]$. Thus, depending on iron content, the effective signal decay of water far exceeds lipid for a given TE, making the water spectra the primary contributor to accurate lipid content measurements.

In the above example for lipid and water constituents, the MRS lipid content measurement is also sensitive to differences in lipid and water T1 values. But this effect is dependent on the TR, a value that typically exceeds 2000 ms (see, for example, Bernard, C P, et al., *J Magn Reson Imaging*. January 2008;27(1):192-7; Chang, J S, et al., *AJR Am J Roentgenol*. July 2006;187(1):W103-6; Machann, J, et al., *Magn Reson Med*. April 2006;55(4):913-7; Longo, R, et al., *J Magn Reson Imaging*. May-June 1995;5(3):281-5; 1995, Szczepaniak L S, et al., *Am J Physiol*. May 1999;276(5 Pt 1):E977-89; Szczepaniak L S, et al., *Am J Physiol Endocrinol Metab*. February 2005;288(2):E462-8), which normally negates significant T1 effects. If the longest constituent T1 is greater than about 800 ms, the MR signal for that component can be shown to recover to approximately 91% and 97% of its equilibrium signal intensity after 2000 and 3000 ms, respectively. As tissue water is associated with these longer T1s, water spectral amount can be saturated successively over multiple TRs, as explained by the following equation (from Haacke, E. M., et al., *Magnetic Resonance Imaging: Physical Principles and Sequence Design*, Wiley-Liss, New York, 1999):

$$M_z = M_0\frac{(1-\exp(-R1\cdot TR))}{1-\cos\alpha\cdot\exp(-R1\cdot TR)} = M_0(1-\exp(-TR\cdot R1)), \quad [3]$$

which is valid for flip angle $\alpha=90$ and TR>>TE and TM. $M_z$ represents the amount of longitudinal signal available for acquisition per TR. Hence, accuracy of lipid content is further improved with knowledge of water and lipid T1 values, especially for short TR. In contrast to $M_z$ recovery normally exceeding 90%, a standard TE of 30 ms produces magnetization less than 65% of equilibrium (using T2<70 ms). Therefore, T2 effects typically outweigh T1 effects in almost all MRS applications. MRS acquisition can be performed in a "single-shot" mode, without dependence on TR.

As measurement times are finite positive values in MR spectroscopy measurement sequences, such as Point-Resolved Spectroscopy (PRESS) and Stimulated Echo Acquisition Mode (STEAM) acquisitions, there are inherent signal losses at the point of acquisition that are unique to the constituent protons. This affects subsequent constituent content calculations in a nontrivial manner, especially if the T1 of constituent components differ from each other or the T2 of constituent components differ from each other.

In practice, T1 and T2 values are unknown in vivo. Depending on the region of interest in a sample, T1 or T2 effects could dominate, or, T1 and T2 effects could be equally important. For robust implementation of MR spectroscopic techniques in a clinical setting, correction of the relaxation effects can be used, as these effects are unknown and can significantly alter lipid content calculations.

A substance having a positive magnetic susceptibility in the sample can be quantified by calculating a ratio of a non-equilibrium signal intensity for a selected spectral component to a sum of all spectral component non-equilibrium signal intensities and by comparing the equilibrium ratio to the non-equilibrium ratio. Optionally, the substance having a positive magnetic susceptibility is iron.

Referring to the flow chart 250 in FIG. 2B, a content of a spectral component can be calculated from the processed, measured MR data without correcting for relaxation effects (step 252). A non-corrected content of a spectral component can be calculated by using signal intensities that are not equilibrium values and are the signals measured at a non-zero value of TE: $C_A = S_A/(S_B+S_A) \times 100$, in which $S_A$ represents a non-equilibrium signal intensity for a spectral component A (measured at a given TE) and $S_B$ represents the sum of non-equilibrium signal intensities for one or more additional identified spectral components in the spectrum (measured at the same TE as $S_A$).

The corrected spectral component content (obtained in step 208) and the uncorrected content of a spectral component (obtained in step 252) can be compared (step 254) and can provide an estimate of an amount of a substance having a magnetic susceptibility (e.g., iron, gadolinium contrast agents) in the sample (step 256). This estimate can be based on previous measurements of samples (e.g., phantoms, biopsied tissue) with a known amount of substance having a magnetic susceptibility, The quantification of the selected spectral component comprising lipid and the quantification of iron content within the sample can be processed simultaneously to provide a simultaneous assessment of fat (i.e., lipid) and iron content in the sample. For example, the lipid and iron content can be assessed simultaneously for a liver sample, including the full liver, or a portion thereof. Thus, the methods can be used to assess fatty liver disease in a subject.

The methods can be executed using an MR system. Example commercial MR systems that can be used include for example, those available from Bruker BioSpin (Billerica, Mass.), Siemens Medical Solutions (Malvern, Pa.), or GE Healthcare Technologies (Milwaukee, Wisc.).

Figure 3:
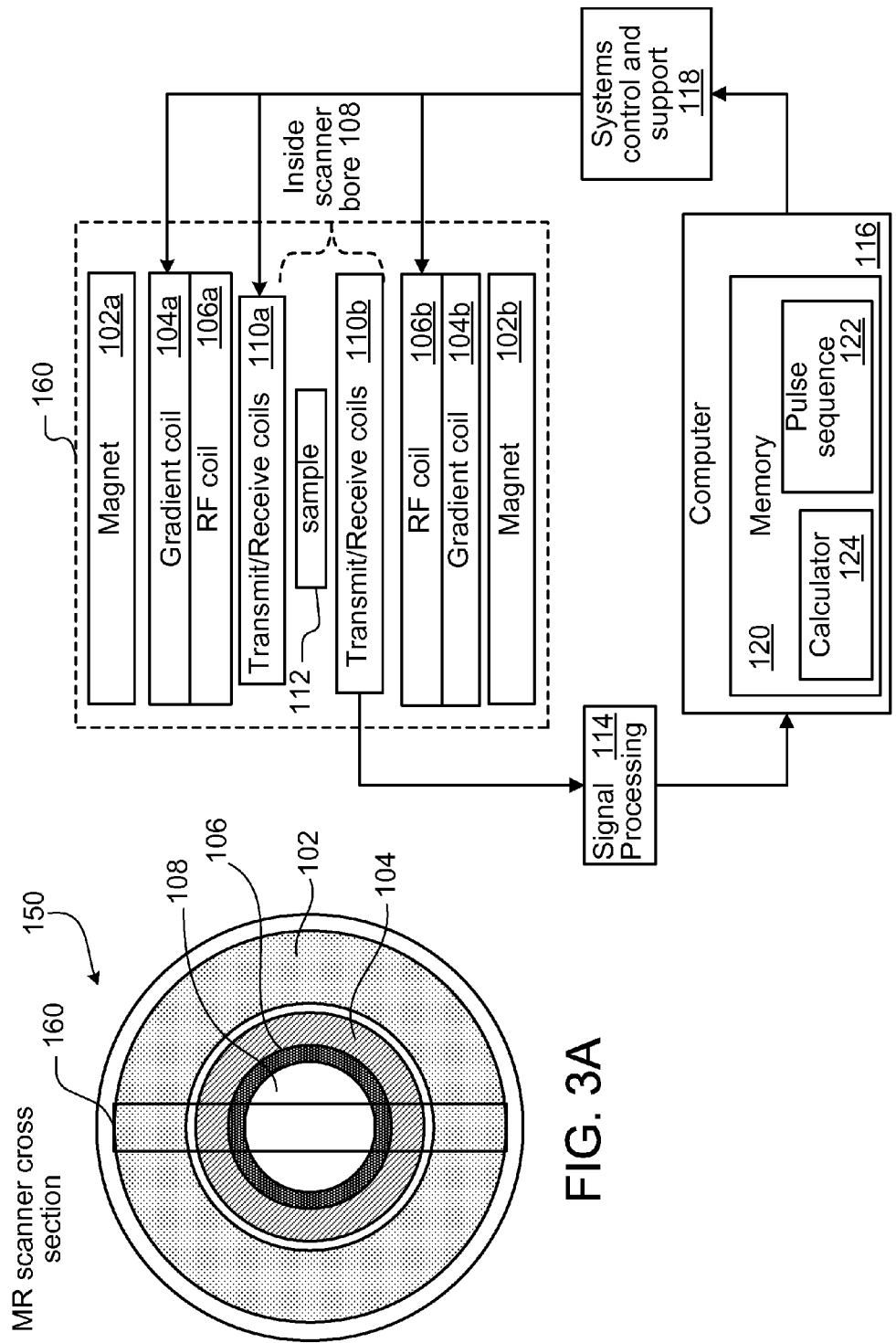
FIGS. 3A and 3B are schematic diagrams illustrating portions of an example magnetic resonance system.

Portions of an example MR system that can be used are schematically illustrated in FIG. 3A and FIG. 3B. FIG. 3A illustrates a schematic cross-sectional view of an example magnetic resonance (MR) scanner 150 that includes a magnet 102, a gradient coil 104, a radiofrequency (RF) coil 106, and a magnet bore 108. A slice 160 through the cross-section 150 is indicated and is illustrated schematically in FIG. 3B.

The magnet 102 can have a field strength between about 0.5 Tesla and about 11 Tesla or more, for example, 1.5 T, 3 T, 4.7 T, 7 T, 9.4 T. The magnet 102 is designed to provide a constant, homogeneous magnetic field. The gradient coil 104 can include one, two, or three orthogonal, controller magnetic gradients used to acquire image or spectroscopic data of a desired slice by generating an encoded and slice-selective magnetic field. The RF coil 106 can be an integrated transceiver coil or can include both an RF transmit coil and an RF receive coil for transmitting and receiving RF pulses.

FIG. 3B schematically illustrates the slice 160 through the cross-section of the MR scanner 150 and additional components of the MR system 100 and their connectivity. The slice 160 illustrates a top part of the magnet 102a and a bottom part of the magnet 102b, a top part of the gradient coil 104a and a bottom part of the gradient coil 104b, a top part of the RF coil 106a and a bottom part of the RF coil 106b. In addition, shown in the slice 160 are a top part of transmit/receive coils 110a and a bottom part of transmit/receive coils 110b. These transmit/receive coils can surround a sample 112 (e.g., a human, an animal, a specimen) or can be placed above or below the sample. The transmit/receive coils 110a and 110b and the sample 112 are placed within the magnet bore 108. The transmit/receive coils can have a transmit functionality, a receive functionality, or both transmit and receive functionalities. For example, a close-fitting smaller receive coil paired with a larger transmit coil can improve image quality if a small region is being imaged. Various types of coils (e.g., a head coil, a birdcage coil, a transverse electromagnetic or TEM coil, a set of array coils) can be placed around specific parts of a body (e.g., the head, knee, wrist) or can be implemented internally depending on the sample and imaging applications.

In FIG. 3B, the bottom part of transmit/receive coils 110b is connected to signal processing 114, which can include, e.g., pre-amplifiers, quadrature demodulators, analog-to-digital converters. (Alternatively, the top part of transmit/receive coils 110a could be connected to signal processing 114.) The signal processing 114 is connected to a computer 116. A systems control and support 118, which is also connected to the computer 116, can include, e.g., digital-to-analog converters, gradient and RF power systems, power amplifiers, eddy current compensation. The systems control and support 118 is connected to the top part of the gradient coil 104a, the top part of transmit/receive coils 110a, and the bottom part of the RF coil 104b. The systems control and support 118 can also be connected to the bottom part of gradient coil 104b, the bottom part of transmit/receive coils 110b, or the top part of RF coil 104a.

The computer 116 controls the operation of other components of the MR system 100 (e.g., the gradient coil 106, the RF coil 104) and receives MR data. In some embodiments, the computer 116 processes data associated with detected MR signals by executing operations, functions, and the like. The results of this data processing can be stored in memory 120, which can be random access memory (RAM), dynamic RAM (DRAM), static RAM (SRAM), etc. In some implementations, the memory 120 can include one or more storage devices (e.g., hard drives), individually or in combination with memory, for storing measurement data, processes, and other types of information.

In some embodiments, the computer 116 executes operations associated with a pulse sequence 122, and a calculator 124. The pulse sequence 122 is a set of instructions that are executed by various components of the MR system 100. The pulse sequence, which can reside in the memory 120, manages the timing of transmitted radiofrequency and gradient pulses as well as the collection of data.

The calculator 124, which can reside in the memory 120 and can be executable by the computer 116, performs operations (e.g., phasing, filtering, integrating, fitting, regressing) on the data collected from the MR system 100. The example MR system used to perform the methods can include a computer program product that can reside in the computer 116 or that can be implemented using the computer 116. The computer program product can be encoded on a computer-readable medium that is operable to cause a data processing apparatus to perform operations.

The operations can comprise applying to a sample a series or radio frequency pulses to perform the methods described herein. For example, the operations can comprise applying to a sample the HISTO sequence and methods. The operations can comprise the application a series of three radio frequency pulses, wherein the series comprises a first pulse having a sufficient amplitude and duration to cause proton spins in the sample to rotate about 90 degrees around an axis applying at least one magnetic field gradient to the sample, a second pulse having a sufficient amplitude and duration to cause the proton spins in the sample to rotate about 90 degrees around an axis and, a third pulse having a sufficient amplitude and duration to cause the proton spins in the sample to rotate about 90 degrees around an axis. The series of pulses can be repeated three, four, or five times at a temporal spacing that permits measurement of a transverse relaxation rate of the sample.

In another example, the computer program product is operable to cause a data processing apparatus to perform operations comprising applying to a sample a series of three radio frequency pulses, wherein the series comprises a first pulse having a sufficient amplitude and duration to cause proton spins in the sample to rotate about 90 degrees around an axis applying at least one magnetic field gradient to the sample, a second pulse having a sufficient amplitude and duration to cause the proton spins in the sample to rotate about 180 degrees around an axis; and a third pulse having a sufficient amplitude and duration to cause the proton spins in the sample to rotate about 180 degrees around an axis. The series of pulses can be repeated three, four, or five times at a temporal spacing that permits measurement of a transverse relaxation rate of the sample.

The computer program product can be operable to cause a data processing apparatus to perform operations including estimating a transverse relaxation property for at least two spectral components of the sample. To estimate of the transverse relaxation properties the computer program can be operable to cause the data processing apparatus to implement the application of a series of temporally spaced radio frequency pulses and at least one magnetic field gradient to the sample. Following application of the radio frequency pulses and magnetic field, the computer program product can be operable to cause the data processing apparatus to implement detection of a magnetic resonance signal from the sample at multiple predefined measurement times. The computer program product can be further operable to cause the data processing apparatus to implement a frequency-domain representation of the detected magnetic resonance signal at each measurement time to be obtained.

Each frequency-domain representation comprises a plurality of peaks, with each peak corresponding to a spectral component of the sample. The computer program product can be further operable to cause the data processing apparatus to implement the determination of an area beneath at least two peaks in each frequency-domain representation of the magnetic resonance signal and a transverse relaxation property for at least two spectral components is estimated by performing a fitting routine on the determined peak areas.

The computer program product can be further operable to cause the data processing apparatus to implement extraction of equilibrium signal intensities for at least two of the spectral components using the estimated transverse relaxation properties. The computer program product can be further operable to cause the data processing apparatus to implement calculation of s ratio of the equilibrium signal intensity extracted for a selected spectral component to a sum of all the extracted spectral component equilibrium signal intensities to quantify the content of the selected spectral component of the signal from the sample. Optionally, the selected spectral component comprises lipid and the ratio quantifies the lipid content in the sample.

The computer program product can be further operable to cause the data processing apparatus to implement the quantification of a substance having a positive magnetic susceptibility in the sample by calculating a ratio of a non-equilibrium signal intensity for a selected spectral component to a sum of all spectral component non-equilibrium signal intensities and by comparing the equilibrium ratio to the non-equilibrium ratio. Optionally, the substance having a positive magnetic susceptibility is iron. The quantification of the selected spectral component comprising lipid and the quantification of iron content within the sample can be processed simultaneously to provide a simultaneous assessment of fat (i.e., lipid) and iron content in the sample.

EXAMPLES

The invention is further described in the following examples, which do not limit the scope of the invention described in the claims. These examples demonstrate, for example, the influence of tissue relaxation effects, especially T2, on resultant lipid content measurements using MRS. Analyses are performed by comparing routine MRS lipid content measures at specific TE values against T2-corrected data in known lipid phantoms and selected human subjects.

Example 1

Effect of Iron Content on R2 and Measured Lipid Content in Phantoms

To evaluate the influence of T1 and T2 relaxation on water and lipid spectral peaks, and subsequent lipid content measurements, 8 individual "liver phantoms" with known lipid content were constructed. The phantoms comprised water-lipid emulsions having two proportions of lipid (10% and 30% vegetable oil by volume), and doped with increasing amounts of iron (0, 0.1, 0.3, 0.5 mM Ferridex, Berlex, N.J.) to induce T2 variability. Tissue water space was simulated with 2% agar-water gels, and the mixture was contained within 200 ml screw-top tubes. Micelles were produced by the addition of lecithin at a concentration of 2% wt/vol.

A high speed T2-corrected multiple echo 1H-MRS acquisition (HISTO) method was performed on a 1.5 Tesla MRI system (Avanto, Siemens Medical Solutions, Malvern, Pa.) with a surface phased array coil. Planning for MRS was performed with the aid of 3 orthogonal, single-shot T2-weighted images (20 slices, 8 mm thick, 0.8 mm gap, TR/TE=1500/86 ms), and cross-reference lines as position indicators. MRS acquisition was performed with STEAM due to its ability for short TE. For T1 investigation, 3 phantoms (10% lipid/0.1 mM iron, 10%/0.3 mM, 30%/0.1 mM) were analyzed with STEAM using TE=20 ms, TM=10 ms, and TR varied in 1000 ms increments from 500 ms to 7500 ms in separate acquisitions. Other parameters were 30×30×30 mm voxel, 2 preparation scans, 4 averages, 512 points, and bandwidth=1200 Hz/px.

For lipid content MRS measurements, phantom spectroscopy was performed with single-average ("single-shot") STEAM with parameters as listed above, except with TR=3000 ms, 0 preparations, 1024 points, and TE varied from 12 to 72 ms in 12 ms steps. Each TE was collected in a separate acquisition. Three repeated MRS measures of each TE were acquired in similar voxel positions to assess precision.

All phantom MRS spectra were exported off-line for analysis using MATLAB software (MATLAB 7.04.365; The Mathworks, Natick, Mass.). Signal integrals were quantified for water and lipid at each echo time following Fourier transform, phase correction, and low-pass filtering with a cutoff of 240 Hz. The algorithm performed signal integration of water ($H_2O$ at 4.7 ppm) and lipids ($CH_2$ and $CH_3$ at 1.3 ppm and 0.95 ppm, respectively) for each echo time. The resultant signal integral values at each echo time were recorded for each sample, and represented as a time series of relative water and lipid content.

Water and lipid relaxation were quantified with a Matlab program. T1 was evaluated for water and lipid independently by means of a two-parameter least-squares curve fitting algorithm, with TR as the independent variable, and spectra integral values as the dependent variable. With TE assumed fixed, the fitting equation was reduced to $S=S_0*(1-exp(-R1*TR))$, with $S_0$ equivalent to the equilibrium spectral value (weighted by fixed T2 decay), and R1 representing the T1 relaxation rate (1/T1). Goodness-of-fit was expressed with an r-squared value (rsq).

T2 values of water and lipids were calculated by fitting the series of MRS echo data to a mono-exponential curve ($S=S_0*exp(-R2*TE)$). T1 contributions were assumed absent due to the single-shot nature of the employed MRS technique. $S_0$ (the equilibrium value) and R2 (1/T2) were estimated for all experiments, with goodness-of-fit represented by r-squared. Lipid content was calculated by Lipid content=$S_{Fat}/(S_{Fat}+S_{Water})*100$ at each measured TE, as well as "TE=0" using the calculated $S_0$ values for water and lipid. Lipid content measurements using $S_0$ represented the T2-corrected lipid content.

For lipid content measurements, the mean and standard deviation (mean±SD) were calculated for 10% and 30% samples as a function of iron content (to assess precision and iron dependency) and TE value (to assess accuracy and TE dependency). This analysis was also performed for T2-corrected lipid content as a function of iron content. Accuracy as a function of TE and iron content in phantom experiments were represented by a percent error: (True Value−Measured)/(True Value). The resultant data were compared among individual groups using a two-tailed Student's t-test with p=0.05.

The evaluation of T1 recovery revealed water and lipid spectra values of 821.7 and 680.3 ms (rsq=0.98), respectively, for the "baseline" 10%/0.1 mM lipid-iron phantom. For higher amounts of lipid and iron content, the measured T1 decreased measurably. An iron content increase to 0.3 mM produced T1 of 340.8 (−58.5% from baseline) and 243.2 ms (−64.2%) for water and lipid, respectively, while a lipid content increase to 30% from baseline produced a T1 of 591.7 (−28.0%) and 185.2 ms (−72.8%). No observable trends between T1 and iron/lipid content could be realized with this data apart from inverse proportionality.

The spectrum profiles for water and lipid were sufficiently visible at all prescribed TEs using STEAM in single-shot mode. All T2 curve fitting and calculation was achieved with high goodness-of-fit (rsq>0.95), and the results of phantom R2 calculations are given in Table 2 below. Independent variables $R2_{lip}$ and $R2_{wat}$ (from equation 1) were approximately equivalent for 0 mM iron. Thus, the lipid content calculations of equation 1 were unaffected by T2 relaxation, and any practical TE was used.

TABLE 2

Measured Transverse Relaxation Rates in Phantoms

| Lipid (%) | Iron (mM) | R2 Relaxation Rate (s−1) Water | R2 Relaxation Rate (s−1) Lipid |
|---|---|---|---|
| 10% | 0 | 12.2 | 15.6 |
|  | 0.1 | 43.6 | 28.8 |
|  | 0.3 | 96.3 | 21.3 |
|  | 0.5 | 144.3 | 24.9 |
| 30% | 0 | 18.3 | 20.3 |
|  | 0.1 | 44.0 | 23.7 |
|  | 0.3 | 114.8 | 32.4 |
|  | 0.5 | 143.6 | 36.6 |

A global linear relationship was found between R2 of water and iron content, [Fe] ($R2_{wat}$=261.7 [Fe]+18.3 s−1; rsq: 0.98), with no observable dependence on lipid content. For lipid R2, the slope of the linear regression (r2, relaxivity) was reduced (30% lipid: $R2_{fat}$=33.7 [Fe]+20.7 $s^{-1}$; rsq: 0.97); however, this $R2_{fat}$ trend exhibited some dependence on lipid content, with 10% lipid samples revealing minor iron dependence reflected by poor linear regression (10% lipid: $R2_{fat}$=9.1 [Fe]+20.6 s−1; rsq: 0.13). From this data, the r2 relaxivity of [Fe] in water was much greater than in lipid: $r2_{wat}/r2_{fat}$=7.8. Furthermore, the baseline R2 (at 0 mM iron) was found to be essentially equivalent for water and lipid ($R2_{0wat}≈R2_{0fat}$=16.6±3.5 $s^{-1}$).

The resultant T2-corrected lipid content, along with all the measured lipid content at each TE are represented in Table 3 for the 10% and 30% phantoms with varying iron content.

TABLE 3

Lipid Content Measurements With and Without T2-correction

| Lipid Content (LC) | Iron (mM) | LC T2-cor | LC TE = 12 ms | LC TE = 24 ms | LC TE = 36 ms | LC TE = 48 ms | LC TE = 72 ms | Avg LC |
|---|---|---|---|---|---|---|---|---|
| 10% | 0 | 8.7 | 8.1 | 8.6 | 7.7 | 7.4 | 6.9 | 7.8 ± 0.6[a] |
|  | 0.1 | 8.7 | 10.1 | 12.2 | 13.4 | 16.2 | 26.2 | 15.6 ± 6.3 |
|  | 0.3 | 9.0 | 18.0 | 37.1 | 56.7 | 74.0 | 91.4 | 55.4 ± 29.0[a] |
|  | 0.5 | 9.3 | 28.8 | 61.2 | 81.7 | 88.2 | 93.4 | 70.6 ± 26.4[a] |

TABLE 3-continued

Lipid Content Measurements With and Without T2-correction

| Lipid Content (LC) | Iron (mM) | LC T2-cor | LC TE = 12 ms | LC TE = 24 ms | LC TE = 36 ms | LC TE = 48 ms | LC TE = 72 ms | Avg LC |
|---|---|---|---|---|---|---|---|---|
| | Avg (SD) | 9.0 ± 0.3 | 16.3 ± 9.4 | 29.8 ± 24.5 | 39.9 ± 35.4 | 46.5 ± 40.6 | 54.5 ± 44.7 | |
| 30% | 0 | 29.7 | 29.2 | 28.7 | 28.9 | 30.1 | 31.8 | 29.7 ± 1.2 |
| | 0.1 | 27.2 | 32.2 | 38.6 | 43.5 | 49.2 | 62.2 | 45.1 ± 11.4[a] |
| | 0.3 | 34.4 | 57.4 | 80.6 | 90.6 | 94.7 | 97.3 | 84.1 ± 16.2[a] |
| | 0.5 | 33.8 | 64.6 | 83.2 | 87.6 | 89.8 | 90.4 | 83.2 ± 10.7[a] |
| | Avg (SD) | 31.3 ± 3.4 | 45.8 ± 17.8 | 55.0 ± 25.2 | 60.2 ± 28.8 | 63.8 ± 29.5 | 68.6 ± 28.5 | |

[a] $p < 0.05$ vs T2-cor Lipid Content

Overall, in terms of accuracy and precision, it was found that T2-correction of water and lipid MRS spectra for lipid content calculation produced low standard deviations and percent errors <15% (range: 1.0% to 14.5%) for 10 and 30% phantoms with varying iron content, whereas percent errors of uncorrected lipid content ranged greatly between <1% to >800%. Iron content was the primary contributor to inaccurate content measurements without T2-correction, with the amount 0.3 mM resulting in accuracy errors consistently over 75%, regardless of TE. For iron content of 0.1 mM, accuracy was dependent on TE, with the lowest TE values producing the lowest percent errors. This dependency was reflected in the precision measurements for 0.1 mM iron; standard deviation among the series of TE values (12 to 72 ms) was found to be 6.3% (p<0.05) and 11.4% (p<0.01) for 10 and 30% phantoms, respectively. For 0 mM iron content, there was no significant improvement in accuracy using T2-correction for any prescribed TE. However, T2-correction was insensitive to all degrees of iron content, and produced consistent results of 9.0±0.3 (10% error) and 31.3±3.4 (4.3%), which were significantly more precise than uncorrected content using TE>12 ms (p<0.05).

Example 2

Phantom Studies Calculating Lipid Content in the Presence of Iron

Liver phantoms containing known amounts of lipid and iron content were constructed to ascertain the precision and accuracy of using the HISTO sequence and method to correct detected MR signals for relaxation effects. Twelve 200 mL samples within 250 mL sterile screw-top tubes were created. Tissue water space was simulated with 2% agar-water gels to which varying concentrations of iron (Feridex, Berlex, N.J.) (0, 0.1, 0.3, 0.5 mM) and varying percentages of lipids (vegetable oil) (0, 10 and 30% per volume) were added at a pH of 7.00±0.2. Micelles were produced by the addition of 2 g of lecithin in order to emulsify the lipid and reproduce morphological packaging analogous to lipid vacuoles within hepatocytes. The R2 measurements and lipid content were assessed by measuring samples with different known concentrations of lipid and iron.

After initial localizer scans were performed on a 1.5 Tesla MRI system (Avanto, Siemens Medical Solutions, Malvern, Pa.) with a surface phased array coil, water spectra of phantoms were obtained by using a HISTO pulse sequence that is based on the STEAM pattern, using a TR of 3 sec, TM=10 ms and five TEs (12, 24, 36, 48 and 72 ms). For the high iron concentrated phantoms, TEs used were 12, 15, 18, 21 and 24 ms. 1024 points were acquired at a bandwidth of 1200 Hz with one signal accumulation using a voxel size of 30×30×30 mm3. The acquisition of 5 echoes took 15 s to acquire. The HISTO pulse sequence was performed in 12 agar-water phantoms containing known amounts of lipid and iron to assess the precision and accuracy of the HISTO correction method. Spectra were formed from the measured MR data and analyzed with custom MATLAB-based software. A mono-exponential curve was fit to the spectral integrals obtained at multiple TE's using the equation $S = S_0 \times \exp(-R2 \times TE)$ to estimate both R2 and $S_0$, for water and lipid signals.

Table 4 lists the results of the estimated lipid content, with and without T2 correction, in the phantoms, which were known to be 10% and 30% lipids content.

TABLE 4

Calculation of lipid percentage in phantoms.

| Phantom | lipid % T2 corrected | lipid % TE = 12 ms |
|---|---|---|
| 10% lipids 0 mM iron | 10.96 | 10.13 |
| 10% lipids 0.1 mM iron | 11.61 | 11.86 |
| 10% lipids 0.3 mM iron | 9.06 | 17.97 |
| 10% lipids 0.5 mM iron | 9.36 | 28.81 |
| 30% lipids 0 mM iron | 29.70 | 29.19 |
| 30% lipids 0.1 mM iron | 27.23 | 32.15 |
| 30% lipids 0.3 mM iron | 34.35 | 57.36 |
| 30% lipids 0.5 mM iron | 33.80 | 64.66 |

Figure 4:
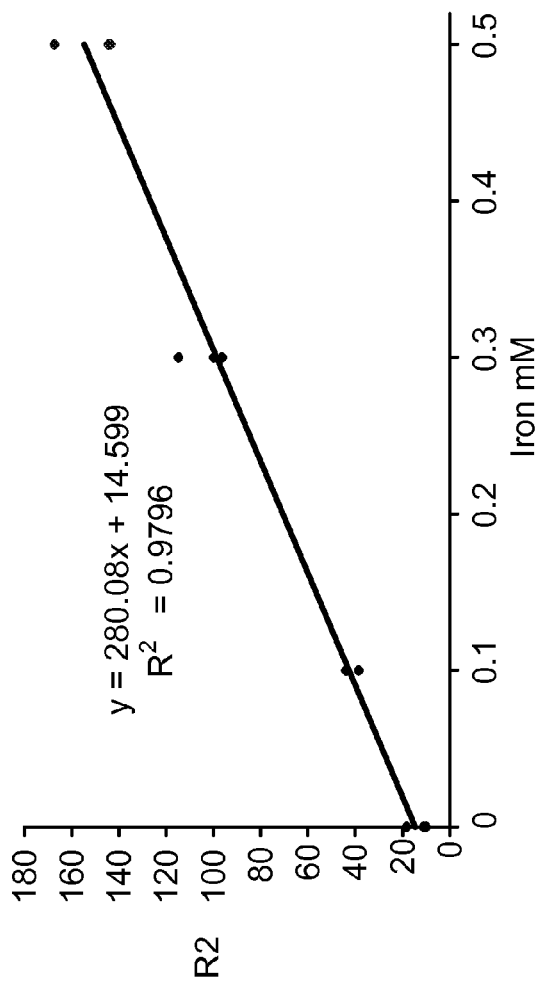
FIG. 4 is a graph of a linear regression.

Percent lipid calculated with a STEAM (TE=12 ms) pulse sequence that is not corrected for relaxation effects shows a large bias as the iron content increases. However, the estimates obtained with a HISTO method that uses a T2 correction remain relatively stable. As seen in FIG. 4, the R2 value of water in the phantoms is correlated with the amount of iron in the sample. Regression analysis revealed a highly significant linear relationship: $R2 = 280.08 \times [Fe] + 14.60$ (rsq=0.9796, p<0.001), with [Fe] in units mM and R2 in $s^{-1}$. The standard error in R2 is 8.46 $s^{-1}$. The intercept (14.60) represents the average R2 of agarose without iron across the 3 different percentages of fat. The lipid content derived with S0 was accurate for all iron concentrations. Without T2 correction, the calculated lipid content exhibits a significant bias that increased with TE and iron level. For TE=12 ms, the error in the calculated lipid content ranged from 80% to 190% in the phantoms with 0.3 and 0.5 mM iron. For longer TEs this error became more severe, because of the different T2 effects in water and lipids.

Low lipid content measured was generally associated with less precision (Table 4). This is likely attributable to the "single-shot" MRS mode, which exacerbates baseline noise.

This usage was motivated by the need to acquire multiple TE in an expedited fashion. For higher lipid content, repeated measurements with the "single-shot" configuration produced excellent precision in all cases.

The multiple echo acquisitions was repeated in the phantoms three times, during the same day, with the same position, acquisition parameters and shimming values to evaluate the reproducibility of the results. In the "10% lipids 0.3 mM iron" phantom the means and standard deviations of the $R2_{wat}$ and lipid content were 106.25 (0.45) and 10.77 (0.14), respectively, and in the "30% lipids 0.3 iron" phantom the values were 122.8 (0.46) and 31.33 (0.14), respectively. For the measurements performed on three different days, the means and standard deviations of the $R2_{wat}$ and lipid content were 103.9 (2.35) and 11.48 (0.84) for the "10% lipids 0.3 mM iron" phantom and 122.48 (0.46) and 32.24 (2.77) for the "30% lipids 0.3 iron" phantom. The pooled standard deviations of $R2_{wat}$ were 0.31 $sec^{-1}$ and 0.60 $sec^{-1}$ for the "10% lipids 0.3 mM iron" and the "30% lipids 0.3 iron" phantoms respectively, and the pooled standard deviations for the lipid content were 0.10% and 0.95%. These findings showed a high degree of intra and inter session reproducibility.

Example 3

Calculating Lipid Content in Human Liver

A total of 12 subjects participated in this investigation. Four subjects (4 male; range: 26-31 yrs) were volunteers and had no prior diagnostic history for fatty liver, but showed indication of abnormal lipid content from a separate study using standard opposed phase MR imaging. Eight subjects (7 males; 13.0±2.4 yrs; range: 11-17 yrs) were pediatric patients recruited in part of a larger cross-discipline non-alcoholic fatty liver disease study being conducted at our institution.

All experiments were performed on a Siemens 1.5 T Avanto system with dedicated anterior-posterior phased-array surface coils. Planning for MRS was performed with the aid of 3 orthogonal, single-shot T2-weighted images (20 slices, 8 mm thick, 0.8 mm gap, TR/TE=1500/86 ms), and cross-reference lines as position indicators. MRS acquisition was performed with a STEAM pulse sequence due to its ability to have a short TE. For T1 investigation, two subjects were analyzed with a STEAM pulse sequence using TE=20 ms, TM=10 ms, and TR varied in 1000 ms increments from 500 ms to 7500 ms in separate acquisitions. Other parameters were 30×30×30 mm voxel, 2 preparation scans, 4 averages, 512 points, and bandwidth=1200 Hz/px. For longer TR acquisitions in vivo, averages were reduced to 2-3 for breath holding purposes.

For constituent content MRS measurements, in vivo spectroscopy was performed with a single-average ("single-shot") STEAM pulse sequence with parameters as listed above, except with TR=3000 ms, 0 preparations, 1024 points, and TE varied from 12 to 72 ms in 12 ms steps. It has been shown with this study that this practice is a feasible and accurate option for breath hold MRS of large spectral peaks such as water and lipid. Each TE was collected in a separate acquisition. Voxel placement was usually in the right lobe, with care taken to avoid large vessel contamination on the orthogonal scout images. The TE array for the STEAM pulse sequence was as noted above for phantoms, with each TE acquired in separate, short breath hold acquisition of 3 seconds. Three repeated MRS measures of each TE were acquired in similar voxel positions to assess precision.

Human MRS spectra was exported off-line to a user-independent fitting routine package (LCModel version 6.1-A). The software was specially configured to fully analyze the spectra knowing that there were only lipid (and water) and possibly choline signals, plus possible signals in the 3.4-3.8 ppm region (sometimes attributed to glycogen and other metabolites). For human data, the resultant integral values for lipid and water spectral components at each echo time were recorded for each sample, and represented as a time series.

Water and lipid relaxation were quantified with a Matlab program. T1 was evaluated for water and lipid independently by means of a two-parameter least-squares curve fitting algorithm, with TR as the independent variable, and spectra integral values as the dependent variable. With TE assumed fixed, the fitting equation was reduced to $S=S_0*(1-\exp(-R1*TR))$, with $S_0$ equivalent to the equilibrium spectral value (weighted by fixed T2 decay), and R1 representing the T1 relaxation rate (1/T1). Goodness-of-fit was expressed with an r-squared value.

T2 values of water and lipids were calculated by fitting the series of MRS echo data to a mono-exponential curve ($S=S_0*\exp(-R2*TE)$). T1 contributions were assumed absent due to the "single-shot" nature of the employed MRS technique. $S_0$ (the equilibrium value) and R2 (1/T2) were estimated for all experiments, with goodness-of-fit represented by r-squared. Lipid content was calculated by content=$S_{Fat}/(S_{Fat}+S_{Water})*100$ at each measured TE, as well as "TE=0" using the calculated $S_0$ values for water and lipid content measurements using $S_0$ represented the T2-corrected content.

For in vivo comparative analysis, repeated content measures were averaged, and uncorrected values at each TE were compared to T2-corrected values using a paired two-tailed Student's t-test with p=0.05. Similarly, the cumulative average lipid content from TE=12 to 72 ms was compared to T2-corrected content. As a measure of precision, the coefficient of variance (CV) was defined as: CV=SD/Avg, for both intra-subject repeated content measurements and across the TE series. A t-test was used to determine significant variabilities between T2-correction and uncorrected content measurements (p=0.05)

One subject did not reveal detectable amounts of lipid on MRS, leaving 11 subjects for analysis. T2-corrected in vivo content measures are given in Table 5, along with standard deviation representing measurement precision of 3 repeated acquisitions.

TABLE 5

Lipid % Measurements in Humans With and Without T2-Correction

| Subj** | Lipid % T2-Cor | Lipid % TE = 12 ms | Lipid % TE = 24 ms | Lipid % TE = 48 ms | Avg* Lipid % |
|---|---|---|---|---|---|
| V1 | 13.8 ± 1.9 | 16.9 ± 0.9 | 18.9 ± 1.1[a] | 25.0 ± 0.8[a] | 23.3 ± 6.5[a] |
| V2 | 5.7 ± 0.2 | 6.5 ± 0.2[a] | 5.8 ± 0.6 | 8.2 ± 0.1[a] | 7.8 ± 2.5 |
| V3 | 3.5 ± 1.6 | 3.7 ± 1.4 | 2.7 ± 1.0 | 3.6 ± 0.7 | 3.6 ± 0.8 |
| S4 | 23.5 ± 0.7 | 25.7 ± 0.4[a] | 26.5 ± 0.1[a] | 31.8 ± 0.4[a] | 32.0 ± 8.5 |

TABLE 5-continued

Lipid % Measurements in Humans With and Without T2-Correction

| Subj** | Lipid % T2-Cor | Lipid % TE = 12 ms | Lipid % TE = 24 ms | Lipid % TE = 48 ms | Avg* Lipid % |
|---|---|---|---|---|---|
| S5  | 18.2 ± 0.4 | 19.5 ± 0.3$^a$ | 18.8 ± 0.4      | 21.4 ± 0.7$^a$ | 22.1 ± 4.5 |
| S6  | 31.6 ± 1.0 | 35.7 ± 1.0$^a$ | 38.0 ± 0.9$^a$  | 46.4 ± 1.1$^a$ | 43.4 ± 7.7$^a$ |
| S7  | 18.3 ± 0.3 | 21.1 ± 0.2$^a$ | 23.7 ± 0.4$^a$  | 29.5 ± 0.3$^a$ | 27.7 ± 6.5$^a$ |
| S8  | 20.9 ± 0.5 | 23.8 ± 0.2$^a$ | 25.5 ± 0.7$^a$  | 31.9 ± 0.7$^a$ | 30.0 ± 6.5$^a$ |
| S9  | 19.6 ± 0.6 | 21.7 ± 0.6$^a$ | 22.5 ± 1.4$^a$  | 27.0 ± 1.6$^a$ | 25.9 ± 4.8$^a$ |
| S10 | 18.5 ± 0.6 | 20.1 ± 0.6$^a$ | 21.2 ± 0.6$^a$  | 23.8 ± 0.2$^a$ | 23.1 ± 3.3$^a$ |
| S11 | 26.7 ± 0.5 | 30.3 ± 0.5$^a$ | 33.0 ± 0.1$^a$  | 40.9 ± 0.4$^a$ | 38.2 ± 8.0$^a$ |

*Mean Lip % for TE = 12 to 72ms.
**V = volunteer; S = patient subject
$^a$p < 0.05 vs. T2-cor Lip %

Also shown in Table 5 are representative uncorrected content measurements for TE=12, 24 and 48 ms. The T2-corrected content was significantly different (p<0.05) than uncorrected content in 83.6% of all group-wise comparisons (46/55), while showing significant difference in 90.9% of comparisons (20/22) when uncorrected content TE>48 ms. The dependency of content measurement on TE is shown in the last column, which is the average and deviation of all TE values (12 to 72 ms). In comparison to T2-corrected content, uncorrected content was significantly different (p<0.05) in 7 of 11 subjects. In two cases where no significant difference was found, the estimated content was less than 10%. The overall average coefficient of variance for content measures using TE=12 to 72 ms was 22.3±5.1%, signifying a lower degree of precision compared to T2-corrected CV, 7.5±12.8% (p<0.05).

Measurement precision of 3 repeated MRS acquisitions with the prescribed TE series was sufficiently high in all subjects for both T2-corrected and uncorrected content. The CV was less than 10% in all cases except volunteer 3.

Example 5

Comparison of HISTO to STEAM In vivo

Sixteen male pediatric patients (average age=13.6 years with a standard deviation of 2.4 years) with known non-alcoholic fatty liver disease (NAFLD) were investigated in this study. To estimate the intra-subject variability of the technique we performed repeated MRS acquisitions of the same subject in three healthy male volunteers (31, 29, and 26 years).

Figures 5A, 5B, 5C:
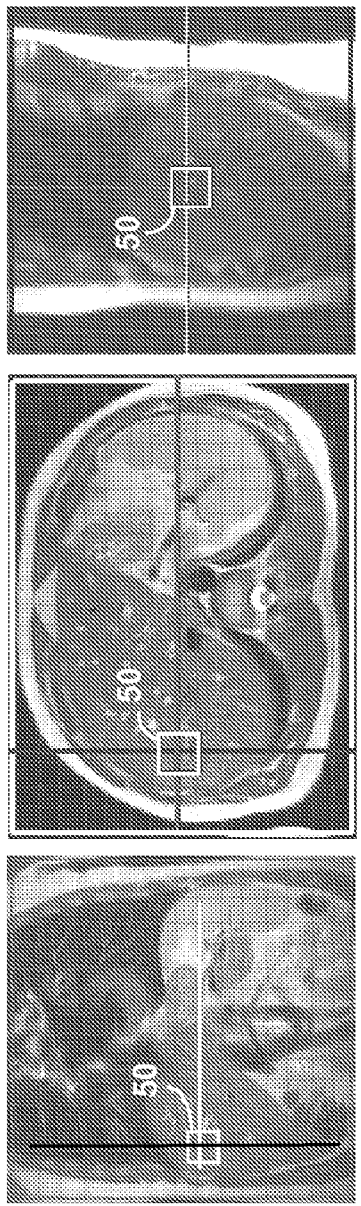
FIGS. 5A-C are magnetic resonance images showing placement of a volume element (voxel) within a subject.

MR signals were detected using a high speed T2-corrected multiple echo $^1$H-MRS acquisition (HISTO) pulse sequence on a 1.5 Tesla MRI system (Avanto, Siemens Medical Solutions, Malvern, Pa.) with a surface phased array coil. The HISTO pulse sequence was applied to human participants and MR signals were detected in 2 different locations using voxels (30×30×30 mm$^3$) placed either in the right posterior (segment 7), right anterior (segment 8), or left lateral (segment 2) liver segments, away from portal and hepatic veins (FIGS. 5A-C). Each measurement was acquired using a HISTO pulse sequence that detected MR signals at 5 echo times (TEs) and was accomplished during a single breath hold.

MR signals were detected using a conventional STEAM pulse sequence for comparison and validation in 4 patients (ages 16, 11, 14 and 16 years). The STEAM sequence and the HISTO pulse sequence were applied in identical liver locations. The HISTO pulse sequence was applied in two different positions for each participant. Detection of MR signals from the STEAM pulse sequence consisted of five different acquisitions (five different breath holds), each using one of the TEs used in the detection of MR signals using the HISTO pulse sequence. The TR, bandwidth, sampling points, signal accumulations and TE values were the same for both acquisitions. The parameters applied were optimized for clinical application (TR/TM 3000/10 and TE=12, 24, 36, 48 and 72 ms). The shimming procedure was redone for each sequence.

Comparison of MR signals detected from the STEAM pulse sequence with MR signals detected from the HISTO sequence was performed partly to account for T1 effects and allowed validation of adequate TR and signal recovery when using the HISTO pulse sequence. Selection of an adequate TR in the HISTO pulse sequence was made based on liver T1 measurements from a volunteer with TE=30 ms and TR values 0.6, 1, 2.5, 5, 10, 20 s, showing a T1 (water) of 747.4 ms. With TR=3 sec. the effects on signal saturation from incomplete T1 relaxation are minimized to 3%. The signal of a specific metabolite in the STEAM pulse sequence is characterized by:

$$\sigma^{metabolite} = S^{metabolite} \times f^{metabolite}_{T1} \times f^{metabolite}_{T2} \qquad [\text{Eq. 1}]$$

in which $$f_{T2} = \exp(-TE/T2) \qquad [\text{Eq. 2}]$$

and $$f_{T1} = [1 - \exp(-Tr_{STEAM}/T1)] \times \exp(-TM/T1) \qquad [\text{Eq. 3}]$$

with $$Tr_{STEAM} = TR - TM - TE/2 \qquad [\text{Eq. 4}]$$

With the values of TR, TM, TE and T1 for the water signal, $f_{T1}$=0.97, indicating that the T1 effect at TR=3 s is negligible.

For the post-processing of the in vivo data, we used LCModel version 6.2-0 (S. Provencher, Oakville, Canada). The analysis of the spectrum is performed in the frequency domain using a linear combination of model spectra. Setting the "SPTYPE" variable equal to "liver-1", the software analyzed the spectra assuming that there is only lipid (and water) and possibly choline signals, plus possible signals in the 3.4-3.8 ppm region (sometimes attributed to glycogen and other metabolites).

The single echo acquisition and the multiple echo acquisition showed no significant differences in corrected lipid level calculations in humans (p=0.5 in patients and p=0.297 in healthy controls). The T2-corrected percentage of lipids and $R2_{wat}$ calculated in the 3 healthy controls (Table 7) and in 4 patients (Table 8); the values obtained with both pulse sequences (STEAM and HISTO) are similar.

TABLE 7

STEAM sequence and HISTO sequence results in volunteers

| Volunteer | | STEAM Pos. 1 | FB Pos. 1 | HISTO Pos 1 | HISTO Pos. 2 |
|---|---|---|---|---|---|
| 1 | R2 fat | 16.96 (0.37) | 14.36 | 16.81 (0.40) | 17.87 (0.85) |
| | R2 water | 31.88 (0.47) | 27.30 | 33.40 (0.14) | 32.60 (0.55) |
| | lipid % | 13.78 (1.89) | 13.83 | 14.31 (0.97) | 13.01 (0.55) |
| 2 | R2 fat | 27.11 (3.83) | 27.23 (1.89) | 25.50 (2.56) | 24.88 (1.58) |
| | R2 water | 33.45 (1.62) | 28.82 (1.89) | 32.28 (1.14) | 29.36 (1.75) |
| | lipid % | 5.71 (0.20) | 5.55 (1.26) | 5.57 (0.68) | 5.44 (0.51) |
| 3 | R2 fat | 27.91 (7.69) | 29.69 (19.35) | 24.40 (14.61) | 31.53 (11.94) |
| | R2 water | 28.33 (0.37) | 27.20 (1.48) | 27.15 (0.13) | 26.48 (1.25) |
| | lipid % | 3.48 (1.55) | 3.27 (2.29) | 4.07 (2.30) | 5.65 (4.09) |
| Pooled std. dev. | R2 fat | 4.97 | | 8.56 | 6.97 |
| | R2 water | 1.00 | | 0.67 | 1.28 |
| | lipid % | 1.42 | | 1.50 | 2.40 |

TABLE 8

STEAM sequence and HISTO sequence results in patients.

| Patient | | STEAM Pos. 1 | HISTO Pos. 1 | HISTO Pos. 2 |
|---|---|---|---|---|
| 1 | R2 fat | 17.24 | 17.15 (0.49) | 17.10 (0.62) |
| | R2 water | 26.93 | 26.24 (0.41) | 27.10 (1.27) |
| | lipid % | 22.71 | 23.46 (0.67) | 22.72 (0.32) |
| 2 | R2 fat | 19.06 | 20.95 (0.92) | 19.63 (0.98) |
| | R2 water | 24.42 | 25.35 (0.41) | 24.65 (0.75) |
| | lipid % | 16.61 | 18.18 (0.41) | 16.98 (0.59) |
| 3 | R2 fat | 18.04 | 16.55 (0.71) | 17.54 (0.92) |
| | R2 water | 30.12 | 29.84 (0.37) | 32.19 (1.21) |
| | lipid % | 35.47 | 34.04 (1.42) | 35.16 (0.52) |
| 4 | R2 fat | 17.26 | 15.38 (1.34) | 16.15 (0.44) |
| | R2 water | 31.16 | 31.17 (0.60) | 31.63 (2.29) |
| | lipid % | 33.48 | 36.62 (1.61) | 34.73 (1.80) |

The computed variances (CV) of the computations obtained from the HISTO method for the $R2_{wat}$ range from 1.24% to 8.10% and for lipid content the CV was from 0.37% to 12.24%. Anthropometric data of the 16 patients were evaluated from all patients, including height, weight and body mass index (BMI) (kg/m$^2$) (Table 9).

TABLE 9

Anthropomorphic data of patients with BMI (kg/m$^2$)

| | Age | | BMI (kg/m$^2$) | | lipid % s | | R2 lipid | | R2 water | |
|---|---|---|---|---|---|---|---|---|---|---|
| | min-max | Average (stdev) | min-max | Average (stdev) | Min-max | Average (stdev) | min-max | Average (stdev) | min-max | Average (stdev) |
| males (16) | 11-17 | 13.56 (2.37) | 26.6-36.8 | 32.14 (3.73) | 14.3-36.2 | 23.33 (7.62) | 14.6-21.5 | 16.89 (1.96) | 25.0-32.5 | 28.71 (2.54) |

Example 5

Intra-Subject Variability

To estimate the intra-subject variability, the multiple echo acquisition was performed in 2 different positions in 3 subjects, and in each position, the measures were repeated 3 times for assessing within session measurement variation. This entire procedure was in turn repeated three times for determining inter-session variability. After each session, the subject was taken out of the scanner and off the scanner table, and each new session started with the repositioning of the subject and included all the scanner adjustments, shimming and localization. The pooled standard deviation was computed from the three averages on each of the three subjects.

The effects of free breathing on the HISTO method were tested in 3 volunteers. In each of the 3 volunteers, MR signals were detected from HISTO pulse sequence using a breath hold. Then, additional MR signals were detected with no change in imaging parameters, except that the subject was allowed to continue normal breathing at rest. The breath holding was performed with the subject instructed to stop breathing at the end of an expiration phase in order to more closely reproduce the voxel location for the breath hold and free breathing states.

The value of R2 is dependent on the shimming quality, or the homogeneity of the magnetic field. Therefore the estimate of iron concentration may be affected by variations in shimming. To quantify the error resulting from altered shimming, we applied the spectroscopic measurements in two different positions of the liver (two different shimming adjustments) and measured the intra-subject variability.

Figure 6:
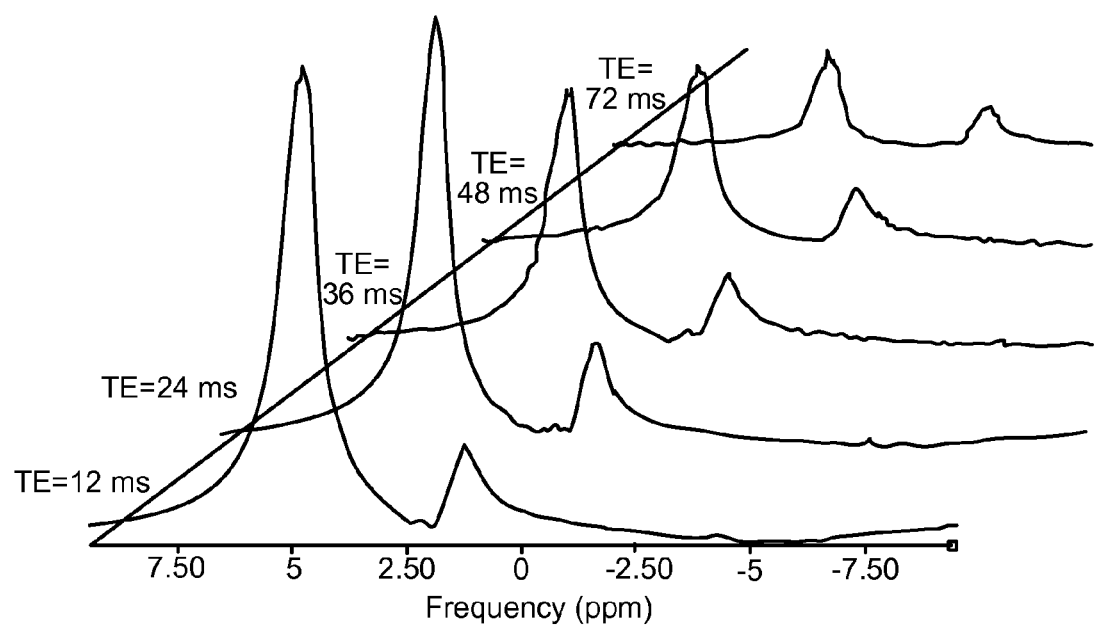
FIGS. 6 and 7 are graphs of magnetic resonance spectra.
Figure 7:
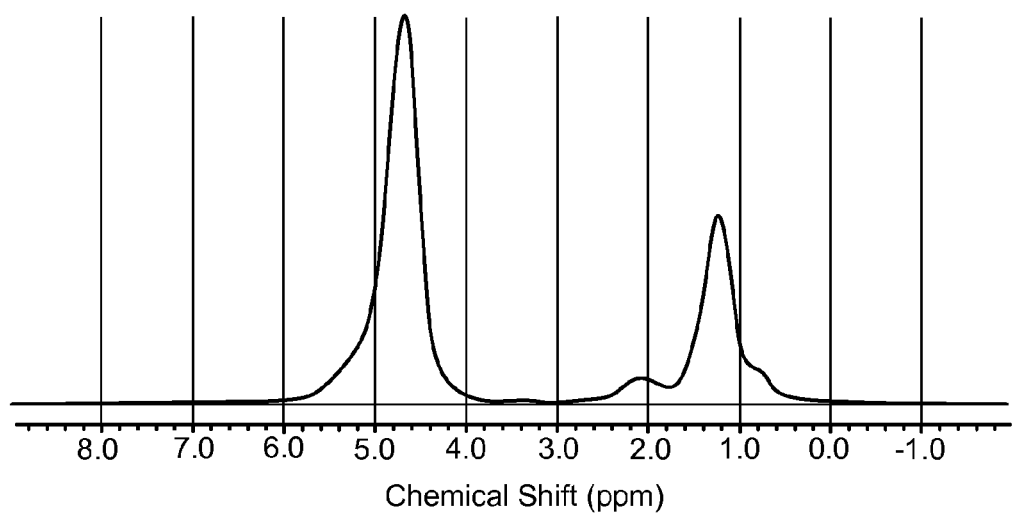

The HISTO method was used in vivo for the measurement of water and lipids in the liver. The TR=3 s. Five TE's, ranged from 12 ms to 72 ms, were applied and TM was 10 ms (FIG. 6—5 echoes). The spectra were analyzed using the LCModel software (FIG. 7—single spectra). To estimate $S_0$ and R2 of water and lipid signals, we fitted to the spectral integrals at multiple TE's a mono-exponential curve, using the equation $S=S_0 \times \exp(-R2 \times TE)$.

The pooled standard deviation was computed from the three averages on each of the 3 healthy subjects. The STEAM and HISTO pulse sequences were repeated in 3 completely new examinations. Table 6 (above) shows the results obtained with the standard STEAM pulse sequence and the HISTO pulse sequence. MR signals were obtained using the HISTO pulse sequence three times in two different positions, and in every repetition the subjects were repositioned on the scanner. The values obtained with the HISTO method are the average of the three repetitions.

The $R2_{wat}$ was very precise in the three healthy volunteers with both pulse sequences (STEAM and HISTO), the maximum standard deviation was 1.75 s$^{-1}$ in position 2, and it was noted that this voxel was always placed near the volunteers' diaphragm. To test the effects of respiratory movement directly, the HISTO pulse sequence was applied with free breathing and compared to breath hold acquisition in 3 volunteers (Table 6). The R2$_{wat}$ without breath holding is lower than the R2 acquired during a breath hold and the standard deviation is increased, however there is not significant differences between the means (p=0.22). While motion from free breathing will alter the R2 determinations, the effects of respiration on R2 do not show significant effects on subsequent lipid % calculations, as we found the T2-corrected lipid levels on the three volunteers for breath hold versus free breathing to be 13.83, 5.55 and 3.27% and 14.31, 5.57 and 4.07%, respectively (p=0.20). In volunteer 1, the measurement in free breathing was performed only once.

For each voxel position the shimming procedure was redone. The effects of shimming differences are shown in Table 7 for 3 in healthy controls and patients in two positions of the voxel in the liver. The standard deviation is very low and the differences between the trials for the fat quantification are ±2% lipid and for the R2$_{wat}$ are ±3 s$^{-1}$. In volunteer #3, the variations of calculated T2-corrected lipid % and R2 of lipids were the largest amongst the three volunteers (Table 7). The pooled standard deviations of R2$_{wat}$ value and lipid % value measured by the HISTO pulse sequence showed the precision of the technique in in vivo.

All results are expressed as mean with their standard deviation (SD). Student's t-test was used for comparison between MR signals detected using the STEAM and HISTO pulse sequences, and between breath-hold and free breathing acquisitions. A p-value of less than 0.05 was considered to indicate a statistically significant difference between groups. For linear regression the Pearson's correlation coefficient R2 was calculated. Pooled standard deviation was calculated to estimate the true standard deviation (precision) in the reproducibility measurements on phantoms and healthy controls.

A number of embodiments have been described. Nevertheless, it will be understood that various modifications may be made without departing from the spirit and scope of the invention. Accordingly, other embodiments are within the scope of the following claims.

What is claimed is:

1. A method for quantifying content of a spectral component of a magnetic resonance signal from a sample comprising:
   estimating a transverse relaxation property for at least two spectral components of the sample by:
   (a) applying a series of temporally spaced radio frequency pulses and at least one magnetic field gradient to the sample using a magnetic resonance (MR) system;
   (b) detecting a magnetic resonance signal from the sample at multiple predefined measurement times;
   (c) obtaining a frequency-domain representation of the detected magnetic resonance signal at each measurement time, wherein each frequency-domain representation comprises a plurality of peaks, each peak corresponding to a spectral component of the sample;
   (d) determining an area beneath at least two peaks in each frequency-domain representation of the magnetic resonance signal; and
   (e) performing via a processor, a fitting routine on the determined peak areas to estimate a transverse relaxation property for at least two spectral components; using the estimated transverse relaxation properties to extract equilibrium signal intensities for at least two of the spectral components; and calculating via a processor, a ratio of the equilibrium signal intensity extracted for a selected spectral component to a sum of all the extracted spectral component equilibrium signal intensities to quantify the content of the selected spectral component of the signal from the sample.

2. The method of claim 1, wherein the selected spectral component is representative of lipid in the sample and the ratio quantifies the lipid content in the sample.

3. The method of claim 1, further comprising quantifying an amount of a substance having a positive magnetic susceptibility in the sample by calculating a ratio of a non-equilibrium signal intensity for a selected spectral component to a sum of all spectral component non-equilibrium signal intensities; and
   comparing the equilibrium ratio to the non-equilibrium ratio.

4. The method of claim 3, wherein the substance having a positive magnetic susceptibility is iron.

5. The method of claim 4, wherein the selected spectral component comprises lipid and the method further comprises a simultaneous quantification of lipid content and iron content within the sample.

6. The method of claim 1, wherein the series of radiofrequency pulses comprises:
   a first pulse having a sufficient amplitude and duration to cause the proton spins in the sample to rotate about 90 degrees around an axis;
   a second pulse having a sufficient amplitude and duration to cause the proton spins in the sample to rotate about 90 or about 180 degrees around an axis; and
   a third pulse having a sufficient amplitude and duration to cause the proton spins in the sample to rotate about 90 or about 180 degrees around an axis.

7. The method of claim 1, wherein the series of three pulses is repeated three, four, or five times.

8. The method of claim 1, wherein a first peak is located at about 4.7 parts per million (ppm).

9. The method of claim 1, wherein a second peak is located between about 1 part per million (ppm) and about 1.5 ppm.

10. The method of claim 1, wherein the sample is part of a mammal.

11. The method of claim 1, wherein the sample is part of a human.

12. The method of claim 1, wherein the sample is a liver.

13. A non-transitory computer readable medium containing computer instructions stored therein a to cause a data processing apparatus to perform operations comprising:
   applying to a sample a series of three radio frequency pulses, wherein the series comprises:
   a first pulse having a sufficient amplitude and duration to cause proton spins in the sample to rotate about 90 degrees around an axis applying at least one magnetic field gradient to the sample;
   a second pulse having a sufficient amplitude and duration to cause the proton spins in the sample to rotate about 90 or 180 degrees around an axis; and
   a third pulse having a sufficient amplitude and duration to cause the proton spins in the sample to rotate about 90 or 180 degrees around an axis; and repeating the series of pulses three, four, or five times at a temporal spacing that permits measurement of a transverse relaxation rate of the sample;
   estimating a transverse relaxation property for at least two spectral components of the sample by:
   (a) applying a series of temporally spaced radio frequency pulses and at least one magnetic field gradient to the sample using a magnetic resonance (MR) system;

(b) detecting a magnetic resonance signal from the sample at multiple predefined measurement times;

(c) obtaining a frequency-domain representation of the detected magnetic resonance signal at each measurement time, wherein each frequency-domain representation comprises a plurality of peaks, each peak corresponding to a spectral component of the sample;

(d) determining an area beneath at least two peaks in each frequency-domain representation of the magnetic resonance signal; and (e) estimating a transverse relaxation property for at least two spectral components by performing a fitting routine on the determined peak areas; using the estimated transverse relaxation properties to extract equilibrium signal intensities for at least two of the spectral components; and calculating a ratio of the equilibrium signal intensity extracted for a selected spectral component to a sum of all the extracted spectral component equilibrium signal intensities to quantify a content of the selected spectral component of the signal.

14. A method for quantifying lipid content within a magnetic resonance signal from a sample comprising:

estimating a transverse relaxation property for at least a lipid spectral component and a water spectral component of the sample by (a) applying a series of temporally spaced radio frequency pulses and at least one magnetic field gradient to the sample using a magnetic resonance (MR) system;

(b) detecting a magnetic resonance signal from the sample at multiple predefined measurement times;

(c) obtaining a frequency-domain representation of the detected magnetic resonance signal at each measurement time, wherein each frequency-domain representation comprises a plurality of peaks, each peak corresponding to a spectral component of the sample;

(d) determining an area beneath at least two peaks in each frequency-domain representation of the magnetic resonance signal, wherein a first peak corresponds to a lipid spectral component and a second peak corresponds to a water spectral component; and (e) estimating via a processor, a transverse relaxation property for at least the lipid and the water spectral components by performing a fitting routine on the determined peak areas; using the estimated transverse relaxation properties to extract equilibrium signal intensities for at least the lipid and water spectral components; and calculating via a processor, a ratio of the estimated equilibrium signal intensity extracted for the lipid spectral component to a sum of the estimated lipid and water equilibrium signal intensities to quantify the lipid content within a magnetic resonance signal from the sample.

15. The method of claim 14, comprising calculating a ratio of a non-equilibrium signal intensity for the lipid spectral component to a sum of the lipid spectral component and the water spectral component non-equilibrium signal intensities; and comparing the calculated equilibrium ratio to the calculated non-equilibrium ratio to quantify an amount of iron in the sample.

16. The method of claim 14, wherein the sample is a human liver.

17. The method of claim 15, wherein a duration between a first radio frequency pulse in the series and a final time of the multiple predefined measurement times is no more than about 15 seconds.

* * * * *